US011242480B2

(12) United States Patent
Moloney et al.

(10) Patent No.: US 11,242,480 B2
(45) Date of Patent: Feb. 8, 2022

(54) THIOL ADDUCTS FOR CORROSION INHIBITION

(71) Applicant: ChampionX USA Inc., Sugar Land, TX (US)

(72) Inventors: Jeremy Moloney, Katy, TX (US); Prakasa Rao Anantaneni, Richmond, TX (US); Ryan Matthew Harrington, Houston, TX (US)

(73) Assignee: ChampionX USA Inc., Sugar Land, TX (US)

( * ) Notice: Subject to any disclaimer, the term of this patent is extended or adjusted under 35 U.S.C. 154(b) by 811 days.

(21) Appl. No.: 16/054,732

(22) Filed: Aug. 3, 2018

(65) Prior Publication Data
US 2019/0040301 A1 Feb. 7, 2019

Related U.S. Application Data

(60) Provisional application No. 62/540,827, filed on Aug. 3, 2017.

(51) Int. Cl.
C09K 8/54 (2006.01)
C23F 11/00 (2006.01)
C23F 11/16 (2006.01)
C07C 323/52 (2006.01)
C07C 323/25 (2006.01)

(52) U.S. Cl.
CPC .............. C09K 8/54 (2013.01); C07C 323/25 (2013.01); C07C 323/52 (2013.01); C23F 11/00 (2013.01); C23F 11/16 (2013.01); C09K 2208/22 (2013.01); C09K 2208/26 (2013.01); C09K 2208/32 (2013.01)

(58) Field of Classification Search
CPC .. C09K 8/54; C09K 2208/22; C09K 2208/26; C09K 2208/32; C07C 323/25; C07C 323/52; C23F 11/00; C23F 11/16
See application file for complete search history.

(56) References Cited

U.S. PATENT DOCUMENTS

| 2,998,462 | A | 8/1961 | Crabb et al. |
| 3,763,048 | A | 10/1973 | Nishihara et al. |
| 4,000,079 | A | 12/1976 | Rasp et al. |
| 4,276,185 | A | 6/1981 | Martin |
| 4,295,979 | A | 10/1981 | Sharp et al. |
| 4,350,600 | A | 9/1982 | Sharp et al. |
| 4,382,002 | A | 5/1983 | Walker et al. |
| 4,450,102 | A | 5/1984 | Lindstrom et al. |
| 4,633,019 | A | 12/1986 | Thompson et al. |
| H1147 | H | 3/1993 | Kennelley et al. |
| 5,213,680 | A | 5/1993 | Kremer et al. |
| 5,853,619 | A | 12/1998 | Watson et al. |
| 6,192,987 | B1 | 2/2001 | Funkhouser et al. |
| 6,365,067 | B1 | 4/2002 | Ahn et al. |
| 6,620,338 | B2 | 9/2003 | Fan et al. |
| 6,645,399 | B2 | 11/2003 | Ahn et al. |
| 7,216,710 | B2 | 5/2007 | Welton et al. |

(Continued)

FOREIGN PATENT DOCUMENTS

| CN | 102321464 A | 1/2012 |
| CN | 105036365 A | 11/2015 |

(Continued)

OTHER PUBLICATIONS

International Search Report and Written Opinion issued for PCT/US2018/045237 dated Oct. 16, 2018, 13 pages.

(Continued)

Primary Examiner — Jeffrey S Lundgren
Assistant Examiner — Ibrahim D Bori
(74) Attorney, Agent, or Firm — Stinson LLP

(57) ABSTRACT

Compounds, compositions and methods are provided for inhibiting corrosion at a surface in the production, transportation, storage, and separation of fluids such as crude oil and natural gas, the compounds having the formula:

$$R_1\diagdown S \diagdown R_2 \quad (1)$$

wherein:
Each $R_1$ is independently —$CH_2OH$ and —$C(O)OH$;
$R_2$ is

[structures shown]

Each $R_3$ is independently hydrogen or $R_5$, or both $R_3$ together form a ring via a linker

[structure shown]

Each $R_4$ is independently hydrogen or $R_5$;
$R_5$ is —$CH_2SC_2H_4R_1$; and
n is an integer from 0 to 3.

15 Claims, No Drawings

(56) References Cited

U.S. PATENT DOCUMENTS

| | | |
|---|---|---|
| 7,972,655 B2 | 7/2011 | Abys et al. |
| 9,238,588 B2 | 1/2016 | Harrington et al. |
| 2004/0170848 A1 | 9/2004 | Ludwig et al. |
| 2005/0079095 A1 | 4/2005 | Crovetto et al. |
| 2005/0169794 A1 | 8/2005 | Welton et al. |
| 2005/0183793 A1 | 8/2005 | Kim et al. |
| 2009/0149356 A1 | 6/2009 | Tiwari et al. |
| 2010/0175583 A1 | 7/2010 | Roschmann et al. |
| 2010/0197136 A1 | 8/2010 | Shimada et al. |
| 2014/0216748 A1 | 8/2014 | Pou |
| 2014/0343332 A1 | 11/2014 | Pou et al. |
| 2015/0037202 A1 | 2/2015 | Harrington et al. |
| 2016/0090655 A1 | 3/2016 | Pou et al. |
| 2016/0230078 A1 | 8/2016 | Pou et al. |
| 2019/0112717 A1 | 4/2019 | Mohr |

FOREIGN PATENT DOCUMENTS

| | | | |
|---|---|---|---|
| CN | 105418509 A | 3/2016 | |
| DE | 30 08 500 A1 | 9/1980 | |
| FR | 2761083 A1 | 9/1998 | |
| JP | H10140379 A | 5/1998 | |
| WO | 00/75399 A2 | 12/2000 | |
| WO | 01/12878 A1 | 2/2001 | |
| WO | 2005/075707 A1 | 8/2005 | |
| WO | 2010/119235 A1 | 10/2010 | |
| WO | 2013/043491 A1 | 3/2013 | |
| WO | 2014/022807 A2 | 2/2014 | |
| WO | WO-2014022807 A2 * | 2/2014 | ............ C07D 498/22 |
| WO | 2015/017385 A2 | 2/2015 | |
| WO | 2016/089459 A1 | 6/2016 | |
| WO | 2016/105381 A1 | 6/2016 | |

OTHER PUBLICATIONS

"Natriumgluconat Produkt Beschreibung," Case No. 527-07-1, ChemicalBook, Dec. 31, 2017, 2 pages, accessed on Jan. 23, 2018 from <http://www.chemicalbook.com/ChemicalProductProperty_DE_CB9229989.htm>.

Talbot, et al., Tetrakishydroxymethylphosphonium Sulfate (THPS) for Dissolving Iron Sulfides Downhole and Topside—A Study of the Chemistry Influencing Dissolution, Paper No. 02030, Corrosion, 2002, pp. 1-14.

Gohar, Camal A. et al., Some [(Substituted Benzylidene) Dithio] Diacetic Acids as Inhibitors for the Acidic Corrosion of Aluminum, Bulletin of Electrochemistry 10 (11-12) Nov.-Dec. 1994, pp. 433-438.

Andreev, N. N., et al., "Laboratory Assessment of Corrosion Inhibitors Effectiveness at Oilfield Pipelines of West Siberian Region. III. Bubble Test," International Journal of Corrosion and Scale Inhibitors, 2013, pp. 17-29, vol. 2, No. 1.

Fujioka, H., et al., "Organic Chemistry Using Weakly Electrophilic Salts: Efficient Formation of O,O-Mixed, O,S- and N,O-Acetals," The Journal of Organic Chemistry, 2007, pp. 7898-7902, vol. 72, No. 21.

Hutnan, M., et al., "Biodegradation of Hexamethylenetetramine in Anaerobic Baffled Reactor," Polish Journal of Environmental Studies, 2005, pp. 585-591. vol. 14, No. 5.

Ibrahim, I. M., et al., "Relative Performance of Isopropylamine, Pyrrole and Pyridine as Corrosion Inhibitors for Carbon Steels in Saline Water at Mildly Elevated Temperatures," International Journal of Scientific & Engineering Research, Feb. 2013, pp. 1-12, vol. 4, No. 2.

Li, J.-X., et al., "Characterization of the Major Odor-Active Compounds in Thai Durian (*Durio zibethinus* L. 'Monthong') by Aroma Extract Dilution Analysis and Headspace Gas Chromatography-Olfactomery," Journal of Agricultural and Food Chemistry, 2012, pp. 11253-11262, vol. 60, No. 45.

Zhou, S.-L., et al., "Two Compounds from the Endophytic *Colletotrichum* sp. of Ginkgo biloba," Natural Product Communications, Aug. 2011, pp. 1131-1132, vol. 6, No. 8.

Gao, Y., et al., Study on Tribological Properties of 2,5-dialkoxymethylthio-1,3,4-thiadiazoles, Wear, 1998, pp. 129-134, vol. 222, No. 2.

SciFinder, CAS Registry No. 2067269-43-4, accessed from <https://scifinder.cas.org/scifinder/view/scifinder/scifinderExplore.jsf> on Dec. 18, 2019, 1 page.

* cited by examiner

THIOL ADDUCTS FOR CORROSION INHIBITION

CROSS REFERENCE TO RELATED APPLICATIONS

This application claims the benefit of U.S. Provisional Patent Application Ser. No. 62/540,827 filed on Aug. 3, 2017, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Corrosion inhibitor compounds and compositions are provided for inhibiting corrosion at a surface of a wellbore or oilfield equipment and for providing protection to the wellbore or equipment against corrosive fluids and gases.

BACKGROUND OF THE INVENTION

One of the greatest risks to oil and gas production infrastructure is accelerated internal pipeline corrosion, particularly as a field ages and water cut rises. The production of oil and gas reservoirs present corrosive environments that place the internal metallurgy of process equipment (e.g., transport pipelines, flow lines, separation equipment), often constructed of mild carbon steel, at risk for failure. The rate of corrosion deterioration in oil and gas field equipment metallurgy is dependent upon production parameters such as oil/water ratio, fluid brine composition, temperature, pH, and the concentration of corrosive gases typically present in the reservoir formation, such as CO2, H2S, or combinations thereof.

In order to preserve the integrity of oil and gas infrastructure, corrosion inhibitors are typically added into the production fluids upstream of piping infrastructure intended to be protected. In general, corrosion inhibitors of this type protect the metal through formation of a passivation film on the metal surface. This passivation layer oil wets the metal surface, which in turn prevents contact of the metal from the corrosive nature of the produced reservoir fluids. Typically, corrosion inhibitor formulations of this type contain a variety of aliphatic organic surfactant molecules ranging from, but not limited to, amines, quaternary amines, imidazolines, phosphate esters, amides, carboxylic acids, or combinations thereof.

Often, organic thiol compounds are added in low concentrations to these corrosion inhibitor components to increase the effectiveness of the traditional corrosion inhibitor molecules. It is believed that these organic thiol molecules create a stronger passivation layer on the metal surface which also increases the persistency of the protective film. In most examples, the sulfur based component consists of a primary thiol/mercaptan (e.g., 2-mercaptoethanol or mercaptoacetic acid). In some instances, however, such thiol based formulations can degrade at elevated temperatures (e.g., during storage at elevated temperatures) to release volatile sulfur-containing vapor/gases (e.g., mercaptans, sulfur dioxide, hydrogen sulfide, and/or carbonyl sulfide).

These volatile sulfur-containing gases are likely created by decomposition of the sulfur-based derivatives, and probably thioglycolic acid, mercaptoalcohols, and the like, decompose to product hydrogen sulfide. This decomposition is a source of environmental and safety problems making the corrosion inhibitors including such sulfur compounds difficult to handle and use.

Thus, despite the availability of corrosion inhibitors for use in the oil and gas industry, there still exists a need for improved compounds, compositions, and methods having reduced toxicity and greater ease of handling.

BRIEF SUMMARY OF THE INVENTION

A class of anti-corrosion compounds are provided, the compounds having the formula:

wherein:
each $R_1$ is independently —$CH_2OH$ and —$C(O)OH$;
$R_2$ is

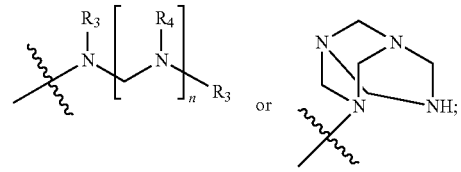

each $R_3$ is independently hydrogen or $R_5$, or both $R_3$ together form a ring via a linker

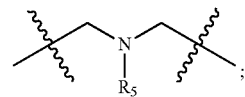

each $R_4$ is independently hydrogen or $R_5$;
$R_5$ is —$CH_2SC_2H_5R_1$; and
n is an integer from 0 to 3.

A composition for inhibiting corrosion at a surface is also provided. The composition includes an effective amount of the compound of formula (1) and a component including an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

A method of inhibiting corrosion at a surface is also provided. The method includes either: contacting the surface with an effective amount of a compound of formula (1) to inhibit corrosion on the surface; contacting the surface with a composition comprising an effective amount of the compound of formula (1) and a component including an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof to inhibit corrosion on the surface; or adding the compound or the composition to a fluid which contacts the surface to inhibit corrosion on the surface.

Other objects and features will be in part apparent and in part pointed out hereinafter.

BRIEF DESCRIPTION OF THE SEVERAL VIEWS OF THE DRAWING

Not applicable.

DETAILED DESCRIPTION OF THE INVENTION

Disclosed herein are compounds and compositions, methods of using the compounds and compositions for inhibiting corrosion, and processes for their preparation. The compounds and compositions are particularly useful for inhibiting corrosion in equipment used in the production, transportation, storage, and separation of crude oil and natural gas. The compositions include a class of thiol-amine corrosion inhibitors that are stable at elevated temperatures when contained in a blended corrosion inhibitor formulation, and show reduced or no volatile degradation species in the vapor phase, unlike that of alkylthiol-based counterparts. As an added benefit, the disclosed thiol-amine compounds do not exhibit the harsh, offensive thiol/mercaptan-based odor typically associated with thiol-containing corrosion inhibitors.

Further, the compounds can advantageously replace the sulfur-containing compounds usually present in corrosion inhibiting compositions, and provide improved storage stability thereby reducing the amount of hydrogen sulfide produced upon storage.

One aspect of the invention is directed to a class of anti-corrosion compounds having the formula:

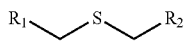
(1)

wherein:
each $R_1$ is independently —$CH_2OH$ and —$C(O)OH$; $R_2$ is

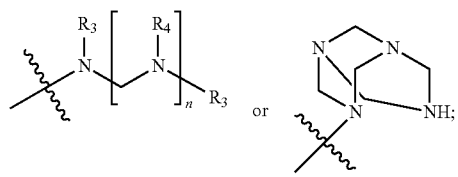

each $R_3$ is independently hydrogen or $R_5$, or both $R_3$ together form a ring via a linker

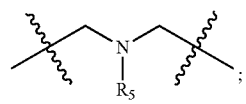

each $R_4$ is independently hydrogen or $R_5$;
$R_5$ is —$CH_2SC_2H_4R_1$; and
n is an integer from 0 to 3.
Preferably, when $R_2$ is

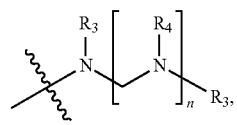

n is 0 and $R_3$ is hydrogen, $R_1$ is —$CH_2OH$.

The compound of formula (1) can have $R_1$ be —$CH_2OH$ or —$C(O)OH$ and $R_2$ be

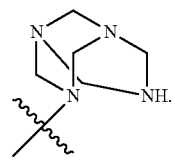

The compound of formula (1) can have $R_1$ be —$CH_2OH$ or —$C(O)OH$; $R_2$ be

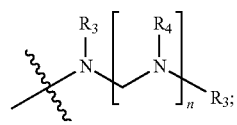

both $R_3$ together form a ring via linker

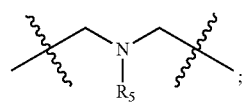

$R_4$ be hydrogen; $R_5$ be —$CH_2SC_2H_4R_1$; and n be 1.

The compound of formula (1) can have $R_1$ be —$CH_2OH$ or —$C(O)OH$; $R_2$ be

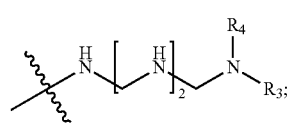

$R_3$ and $R_4$ be $R_5$; and $R_5$ be —$CH_2SC_2H_4R_1$.

The compound of formula (1) can have $R_1$ be —$CH_2OH$ or —$C(O)OH$; $R_2$ be (1) [structure shown]

$R_3$ be hydrogen or $R_5$; $R_5$ is —$CH_2SC_2H_4R_1$; and n be 0 or 1. Preferably, $R_3$ is hydrogen and n is 0, or $R_3$ is $R_5$; $R_5$ is —$CH_2SC_2H_4R_1$; and n is 1.

Representative compounds of formula (1) derived from the reaction of hexamethylenetetramine (HMTA) and 2-mercaptoethanol (2-ME) include:

(2) [structure]

(3) [structure]

(4) [structure]

(5) [structure]

(6) [structure]

(7) [structure]

Representative compounds of formula (1) derived from the reaction of hexamethylenetetramine and thiolglycolic acid (TGA) include:

(8) [structure]

(9) [structure]

(10) [structure]

(11) [structure]

(12) [structure]

(13) [structure]

(14) [structure]

(15) [structure]

The compounds of formula (1) can be prepared by reacting an appropriate thiol compound with hexamethylenetetramine (HMTA) as depicted in the reaction scheme below:

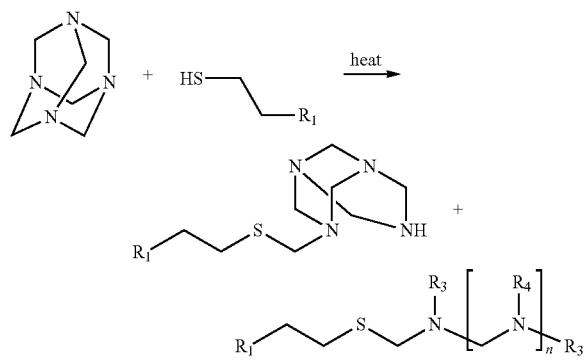

wherein $R_1$, $R_3$, $R_4$, $R_5$ and n are as defined above. When $R_1$ is hydroxy, the compounds of formulae (2)-(8) can be formed. When $R_1$ is carboxyl, the compounds of formulae (9)-(15) can be formed.

The compounds can be prepared, for example, by combining the thiol compound with one or more equivalents of HMTA and an optional solvent such as water or a non-aqueous solvent to form a mixture and heating the mixture at about 50-80° C. until no odor is observed. When the thiol compound is heated, it releases an odor which is no longer detectable when the reaction products are formed.

Alternatively, the compounds can be prepared by combining HMTA and one or more equivalents of the thiol compound with an optional solvent such as water or a non-aqueous solvent to form a mixture and heating the mixture at about 90-120° C. until the mixture becomes homogeneous.

The compounds can also be prepared by heating the thiol compound to about 70-100° C., slowly adding solid HMTA to form a slurry, and heating the slurry at about 80-120° C. until a homogeneous mixture is formed.

The molar ratio of the thiol compound to the HMTA can be, for example, from about 1:30 to about 30:1, about 1:20 to about 20:1, about 1:10 to about 10:1, about 1:1 to about 8:1, about 1:1 to about 6:1, or from about 1:1 to about 4:1.

The compounds and compositions containing the compounds as described below can partially or completely suppress the production of hydrogen sulfide upon storage of the compounds or compositions. Thus, the compounds and compositions containing the compounds have an undetectable amount of hydrogen sulfide upon storage for at least 30 days at a temperature of 25° C.

Another aspect of the invention is a composition for inhibiting corrosion at a surface. The composition comprises an effective amount of the compound of formula (1) and a component comprising an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof. The compound of formula (1) can be one or more of the compounds of formulae (2)-(15), such as a mixture of compounds (2)-(8) or compounds (9)-(15).

The composition can comprise, for example, from about 0.1 to about 20 wt. % of one or more compounds of formula (1) and from about 80 to about 99.9 wt. % of the component; from about 0.1 to about 20 wt. % of one or more compounds of formula (1), from about 1 to about 60 wt. % of the component and from about 20 to about 98.9 wt. % water; from about 10 to about 20 wt. % of one or more compounds of formula (1), from about 30 to about 40 wt. % of the component and from about 40 to about 60 wt. % water; or from about 15 to about 20 wt. % of one or more compounds of formula (1), from about 1 to about 10 wt. % of the component and from about 70 to about 84 wt. % water.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

In addition to the component, the composition can comprise water.

The component of the composition can comprise a corrosion inhibitor in addition to the one or more compounds of formula (1). The composition can comprise from about 0.1 to 20 wt. %, 0.1 to 10 wt. %, or 0.1 to 5 wt. % of the one or more additional corrosion inhibitors, based on total weight of the composition. A composition of the invention can comprise from 0 to 10 percent by weight of the one or more additional corrosion inhibitors, based on total weight of the composition. The composition can comprise 1.0 wt. %, 1.5 wt. %, 2.0 wt. %, 2.5 wt. %, 3.0 wt. %, 3.5 wt. %, 4.0 wt. %, 4.5 wt. %, 5.0 wt. %, 5.5 wt. %, 6.0 wt. %, 6.5 wt. %, 7.0 wt. %, 7.5 wt. %, 8.0 wt. %, 8.5 wt. %, 9.0 wt. %, 9.5 wt. %, 10.0 wt. %, 10.5 wt. %, 11.0 wt. %, 11.5 wt. %, 12.0 wt. %, 12.5 wt. %, 13.0 wt. %, 13.5 wt. %, 14.0 wt. %, 14.5 wt. %, or 15.0 wt. % by weight of the one or more additional corrosion inhibitors, based on total weight of the composition. Each system can have its own requirements, and the weight percent of one or more additional corrosion inhibitors in the composition can vary with the system in which it is used.

The one or more additional corrosion inhibitors can comprise an imidazoline compound, a quaternary ammonium compound, a pyridinium compound, or a combination thereof.

The one or more additional corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The one or more additional corrosion inhibitor component can include an imidazoline of Formula (I):

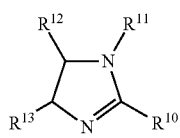

(I)

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$ which is the alkyl mixture typical in tall oil fatty acid (TOFA), and $R^{11}$, $R^{12}$ and $R^{13}$ are each hydrogen.

The one or more additional corrosion inhibitor component can include an imidazolinium compound of Formula (II):

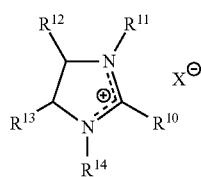

(II)

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The one or more additional corrosion inhibitors can comprise a bis-quaternized compound having the formula (III):

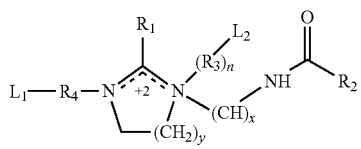

(III)

wherein:

$R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof;

$R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof;

$L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$;

$R_5$ is each independently a branched or unbranched alkyl, aryl, alkylaryl, alkylheteroaryl, cycloalkyl, or heteroaryl group having from 1 to about 10 carbon atoms;

n is 0 or 1, and when n is 0, $L_2$ is absent or H;

x is from 1 to about 10; and y is from 1 to about 5. Preferably, $R_1$ and $R_2$ are each independently $C_6$-$C_{22}$ alkyl, $C_8$-$C_{20}$ alkyl, $C_{12}$-$C_{18}$ alkyl, $C_{16}$-$C_{18}$ alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R_3$ and $R_4$ can be $C_2$-$C_3$ alkylene such as —C$_2$H$_2$—; n is 1 and $L_2$ is —COOH or n is 0 and $L_2$ is absent or H; x is 2; y is 1; $R_3$ and $R_4$ are —C$_2$H$_2$—; and $L_1$ is —COOH.

It should be appreciated that the number of carbon atoms specified for each group of formula (III) refers to the main chain of carbon atoms and does not include carbon atoms that may be contributed by substituents.

The one or more additional corrosion inhibitors can comprise a bis-quaternized imidazoline compound having the formula (III) wherein $R_1$ and $R_2$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (III) wherein $R_1$ and $R_2$ are each independently $C_{16}$-$C_{18}$ alkyl; $R_4$ is —C$_2$H$_2$—; x is 2; y is 1; n is 0; $L_1$ is —COOH, —SO$_3$H, or —PO$_3$H$_2$ and $L_2$ is absent or H.

The one or more additional corrosion inhibitors can be a quaternary ammonium compound of Formula (IV):

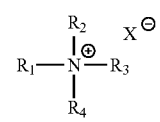

(IV)

wherein $R_1$, $R_2$, and $R_3$ are independently $C_1$ to $C_{20}$ alkyl, $R_4$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$], wherein R$^5$, R$^{6a}$, R$^{7a}$, and R$^{8a}$ contain one to 18 carbon atoms, and X is Cl, Br or I. For the quaternary salts, R$^{5a}$, R$^{6a}$, R$^{7a}$, and R$^{8a}$ can each be independently alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The one or more additional corrosion inhibitor component can comprise a pyridinium salt such as those represented by Formula (V):

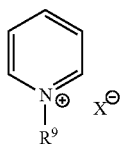

(V)

wherein $R^9$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The one or more additional corrosion inhibitor components can include additional corrosion inhibitors such as phosphate esters, monomeric or oligomeric fatty acids, or alkoxylated amines.

The one or more additional corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The one or more additional corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The one or more additional corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The composition can be substantially free of or free of any organic sulfur compound other than the compound of formula (1). A composition is substantially free of any organic sulfur compound if it contains an amount of organic sulfur compound less than 0.50 wt. % preferably less than 0.10 wt. %, and more preferably less than 0.01 wt. %.

The component of the composition can further include a demulsifier. Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include a paraffin inhibitor. The composition can comprise from about 0.1 to 10 wt. %, from about 0.1 to 5 wt. %, or from about 0.5 to 4 wt. % of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkylsaccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.5 to 20 wt. %, or from about 1 to 10 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 0.1 to 25 wt. %, from about 0.5 to 20 wt. %, or from about 1 to 10 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

Corrosion inhibitor compositions made according to the invention can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the corrosion inhibitors of the invention can be formulated into compositions comprising the following components. These formulations include the ranges of the components listed and can optionally include additional agents.

Another aspect of the invention is a method of inhibiting corrosion at a surface. The method comprises either: contacting the surface with an effective amount of a compound of formula (1) to inhibit corrosion on the surface; contacting the surface with a composition comprising an effective amount of the compound of formula (1) and a component comprising an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof to inhibit corrosion on the surface; or adding the compound or the composition to a fluid which contacts the surface to inhibit corrosion on the surface. The compound of formula (1) can be one or more of the compounds of formulae (2)-(15), such as a mixture of compounds (2)-(8) or compounds (9)-(15). The composition can be any composition as described herein.

The compounds/compositions can be used for inhibiting corrosion in oil and gas applications such as by treating a gas or liquid stream with an effective amount of a compound or composition as described herein. The compounds and compositions can be used in any industry where it is desirable to inhibit corrosion at a surface.

The compounds/compositions can be used in water systems, condensate/oil systems/gas systems, or any combination thereof. For example, the compounds/compositions can be used in controlling scale on heat exchanger surfaces.

The compounds/compositions can be applied to a gas or liquid produced, or used in the production, transportation, storage, and/or separation of crude oil or natural gas.

The compounds/compositions can be applied to a gas stream used or produced in a coal-fired process, such as a coal-fired power plant.

The compounds/compositions can be applied to a gas or liquid produced or used in a waste-water process, a farm, a slaughter house, a land-fill, a municipality waste-water plant, a coking coal process, or a biofuel process.

A fluid to which the compounds/compositions can be introduced can be an aqueous medium. The aqueous medium can comprise water, gas, and optionally liquid hydrocarbon.

A fluid to which the compounds/compositions can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic

| Component | 1 | 2 | 3 | 4 | 5 | 6 | 7 | 8 | 9 | 10 | 11 | 12 |
|---|---|---|---|---|---|---|---|---|---|---|---|---|
| Compound of Formula (1) | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Organic solvent | 5-40 | — | 5-50 | — | 5-50 | 5-50 | 5-40 | — | 5-50 | — | — | 10-20 |
| Additional corrosion inhibitor | 0.1-20 | 0.1-20 | — | — | — | — | 0.1-20 | 0.1-20 | — | — | — | 0.1-20 |
| Asphaltene inhibitor | 0.1-5 | 0.1-5 | 0.1-5 | 0.1-5 | — | — | 0.1-5 | 0.1-5 | 0.1-5 | — | — | 0.1-5 |
| Scale inhibitor | 1-10 | 1-10 | 1-10 | 1-10 | 1-10 | — | 1-10 | 1-10 | 1-10 | 1-10 | — | 1-10 |
| Gas hydrate inhibitor | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | — |
| Water | 0.00 | 0-40 | 0-10 | 0-60 | 0-15 | 0-25 | 0.00 | 0-40 | 0-10 | 0-65 | 0-75 | — |

| Component | 13 | 14 | 15 | 16 | 17 | 18 | 19 | 20 | 21 | 22 | 23 | 24 |
|---|---|---|---|---|---|---|---|---|---|---|---|---|
| Compound of Formula (1) | 0.1-20 | 0.1-20 | 0.1-20 | 0.1-20 | 0.1-20 | 0.1-20 | 10-20 | 10-20 | 10-20 | 10-20 | 10-20 | 10-20 |
| Organic solvent | — | 10-20 | — | 10-35 | 10-35 | — | 10-15 | — | — | 10-35 | 10-35 | — |
| Additional corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene inhibitor | 0.1-5 | — | — | — | — | — | 0.1-5 | — | — | — | — | — |
| Scale inhibitor | 1-10 | 1-10 | — | — | 1-10 | — | 1-10 | 1-10 | — | — | — | 1-10 |
| Gas hydrate inhibitor | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | 0.00 | 0-20 | 0-30 | 0-20 | 0.00 | 0-50 | cracker feeds, gas oil, naphtha, fluid catalytic cracking slurry, diesel fuel, fuel oil, jet fuel, gasoline, and kerosene.

The fluid or gas can be a refined hydrocarbon product.

A fluid or gas treated with a compound/composition can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C. to 90° C. The fluid or gas can be at a temperature of 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. The fluid or gas can be at a temperature of 85° C., 86° C., 87° C., 88° C., 89° C., 90° C., 91° C., 92° C., 93° C., 94° C., 95° C., 96° C., 97° C., 98° C., 99° C., or 100° C.

The compounds/compositions can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the compounds/compositions are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The compounds/compositions can be introduced into a fluid or gas by any appropriate method for ensuring dispersal through the fluid or gas.

The compounds/compositions can be added to the hydrocarbon fluid before the hydrocarbon fluid contacts the surface.

The compounds/compositions can be added at a point in a flow line upstream from the point at which corrosion prevention and/or schmoo removal is desired.

The compounds/compositions can be injected using mechanical equipment such as chemical injection pumps, piping tees, injection fittings, atomizers, quills, and the like.

The compounds/compositions of the invention can be introduced with or without one or more additional polar or non-polar solvents depending upon the application and requirements.

The compounds/compositions can be pumped into an oil and/or gas pipeline using an umbilical line. A capillary injection system can be used to deliver the compounds/compositions to a selected fluid.

A fluid to which the compositions can be introduced can be an aqueous medium. The aqueous medium can comprise water, gas, and optionally liquid hydrocarbon. A fluid to which the compounds/compositions can be introduced can be a liquid hydrocarbon.

The compounds/compositions can be introduced into a liquid and mixed.

The compounds/compositions can be injected into a gas stream as an aqueous or non-aqueous solution, mixture, or slurry.

The fluid or gas can be passed through an absorption tower comprising compounds/compositions.

The compounds/compositions can be applied to a fluid or gas to provide any selected concentration. In practice, the compounds/compositions are typically added to a flow line to provide an effective treating dose of the described compounds from about 0.01 to about 5,000 ppm. The compounds/compositions can be applied to a fluid or gas to provide an actives concentration of about 1 parts per million (ppm) to about 1,000,000 ppm, about 1 parts per million (ppm) to about 100,000 ppm, or about 10 ppm to about 75,000 ppm. The compounds/compositions can be applied to a fluid to provide an actives concentration of about 100 ppm to about 10,000 ppm, about 200 ppm to about 8,000 ppm, or about 500 ppm to about 6,000 ppm. The actives concentration means the concentration of the compounds of formula (1).

The compounds/compositions can be applied to a fluid or gas to provide actives concentration of 0.1 ppm, 0.5 ppm, 1 ppm, 2 ppm, 5 ppm, 10 ppm, 20 ppm, 100 ppm, 200 ppm, 500 ppm, or 1,000 ppm. The compounds/compositions can be applied to a fluid or gas to provide an actives concentration of 0.125 ppm, 0.25 ppm, 0.625 ppm, 1 ppm, 1.25 ppm, 2.5 ppm, 5 ppm, 10 ppm, or 20 ppm. Each system can have its own dose level requirements, and the effective dose level of compounds/compositions to sufficiently reduce the rate of corrosion can vary with the system in which it is used.

The compounds/compositions can be applied continuously, in batch, or a combination thereof. The compounds/compositions doses can be continuous to prevent corrosion. The compounds/compositions doses can be intermittent (i.e., batch treatment) or the compounds/compositions doses can be continuous/maintained and/or intermittent to inhibit corrosion.

Dosage rates for continuous treatments typically range from about 10 to about 500 ppm, or about 10 to about 200 ppm. Dosage rates for batch treatments typically range from about 10 to about 400,000 ppm, or about 10 to about 20,000 ppm. The compounds/compositions can be applied as a pill to a pipeline, providing a high dose (e.g., 20,000 ppm) of the composition.

The flow rate of a flow line in which the compound/composition is used can be between 0 and 100 feet per second, or between 0.1 and 50 feet per second. The compounds/compositions can also be formulated with water in order to facilitate addition to the flow line.

The compounds/compositions can provide corrosion protection at least equivalent to the protection provided by the corresponding thiol compound used in preparing the compound of formula (1).

The compounds/compositions can evolve 250 ppm or less, 200 ppm or less, 150 ppm or less, 100 ppm or less, 50 ppm or less, 30 ppm or less, 25 ppm or less, 20 ppm or less, 15 ppm or less, 10 ppm or less, 9 ppm or less, 8 ppm or less, 7 ppm or less, 6 ppm or less, 5 ppm or less, 4 ppm or less, 3 ppm or less, 2 ppm or less, 1 ppm or less, or 0 ppm of sulfur species into a headspace. The headspace sulfur species concentration can be determined by placing a sample of the compound/composition (e.g., 40 g) into a sealed receptacle (e.g., an 8 ounce glass jar sealed with a cap containing a hole fitted with a rubber stopper which is used for sampling); aging the compound/composition at a selected temperature for a selected time period (e.g., in a 50° C. oven over a period of 10 days); and sampling the headspace for sulfur species (e.g., with detection tubes, such as GasTec sulfur detection tubes). The sulfur species quantified can include hydrogen sulfide, mercaptans (e.g., methyl mercaptan, ethyl mercaptan, and the like), sulfur dioxide, and/or carbonyl sulfide.

The surface can be a part of a wellbore or equipment used in the production, transportation, storage, and/or separation of a fluid such as crude oil or natural gas.

More specifically, the surface can be a part of equipment used a coal-fired process, a waste-water process, a farm, a slaughter house, a land-fill, a municipality waste-water plant, a coking coal process, or a biofuel process. Preferably, the surface can be a part of equipment used in the production of crude oil or natural gas.

The equipment can comprise a pipeline, a storage vessel, downhole injection tubing, a flow line, or an injection line.

The compounds/compositions of the invention can be used for inhibiting corrosion in other applications.

The compounds/compositions are useful for corrosion inhibition of containers, processing facilities, or equipment in the food service or food processing industries. The compounds/compositions have particular value for use on food packaging materials and equipment, and especially for cold or hot aseptic packaging. Examples of process facilities in which the compounds/compositions can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The compounds/compositions can be used to inhibit corrosion in tanks, lines, pumps, and other equipment used for the manufacture and storage of soft drink materials, and also used in the bottling or containers for the beverages.

The compounds/compositions can also be used on or in other industrial equipment and in other industrial process streams such as heaters, cooling towers, boilers, retort waters, rinse waters, aseptic packaging wash waters, and the like. The compounds/compositions can be used to treat surfaces in recreational waters such as in pools, spas, recreational flumes and water slides, fountains, and the like.

The compounds/compositions can be used to inhibit the corrosion of metal surfaces contacted with cleaners in surfaces found in janitorial and/or housekeeping applications, food processing equipment and/or plant applications, and in laundry applications. For example, the corrosion of washers, such as tunnel washers for washing textiles, can be inhibited according to methods disclosed herein.

The compounds/compositions can be used or applied in combination with low temperature dish and/or warewash sanitizing final rinse, toilet bowl cleaners, and laundry bleaches. The compounds, compositions and methods can be used to treat metal surfaces, such as ware, cleaned and/or sanitized with corrosive sources.

The compounds, compositions and methods disclosed herein protect surfaces from corrosion caused by hypochlorite bleach. A method can include providing the corrosion inhibitor compounds/compositions to a surface treated with a hypochlorite solution in order to inhibit corrosion caused by the hypochlorite solution. The method can include preparing an aqueous use composition of the present corrosion inhibitor composition. The method can further include contacting a surface, such as a hard metal surface, in need of corrosion inhibition due to contact with a hypochlorite solution.

The compounds/compositions can be dispensed in any suitable method generally known by one skilled in the art. For example, a spray-type dispenser can be used, such as that disclosed in U.S. Pat. Nos. 4,826,661, 4,690,305, 4,687,121, 4,426,362 and in U.S. Pat. Nos. Re 32,763 and 32,818, the disclosures of which are incorporated by reference herein. A spray-type dispenser functions by impinging a water spray upon an exposed surface of a composition to dissolve a portion of the composition, and then immediately directing the concentrate solution including the composition out of the dispenser to a storage reservoir or directly to a point of use.

The compounds/compositions can be dispensed by immersing either intermittently or continuously in water. The composition can then dissolve, for example, at a controlled or predetermined rate. The rate can be effective to maintain a concentration of dissolved agent that is effective for use according to the methods disclosed herein.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups may be unsubstituted or substituted by one or more suitable substituents, as defined above.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1] heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle" or "heterocyclyl," as used herein, refers to a monocyclic, bicyclic, or tricyclic group containing 1 to 4 heteroatoms selected from N, O, S(O)$_n$, P(O)$_n$, PR$_z$, NH or NR$_z$, wherein R$_z$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "hydroxy," as used herein, refers to an —OH group.

The term "suitable substituent," as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The term "water cut," as used herein, means the percentage of water in a composition containing an oil and water mixture.

Having described the invention in detail, it will be apparent that modifications and variations are possible without departing from the scope of the invention defined in the appended claims.

EXAMPLES

The following non-limiting examples are provided to further illustrate the invention.

Example 1: Reaction of 2-ME with HMTA

Under normal atmospheric conditions, 2-ME (0.0214 mol) and solid HMTA (0.0214 mol) and R-99 (5 g) were combined and let stand at ambient temperature for 30 days before submitting for NMR analysis to determine the extent of reaction. This reaction was repeated and let stand at 50° C. for 30 days and repeated again and let stand at 80° C. for 30 days. After 30 days at ambient temperature, the samples were subjected to NMR analysis. NMR analysis showed consumption of all 2-ME.

The above synthesis was repeated with 2-ME (0.0071 mol) and HMTA (0.214 mol) and let stand at the temperatures and time periods as indicated above. NMR analysis showed consumption of all 2-ME.

Following the above observations, thiol-amine compounds of the invention were synthesized under different reaction conditions. Under normal atmospheric conditions, 2-ME (0.2 mol), solid HMTA (0.2 mol) and water were charged to a suitable volume round bottom flask equipped with a reflux condenser and a magnetic stir bar. The slurry was heated to 90-105° C. under stirring for about 3 h at which time the mixture was homogeneous. The solution was allowed to cool to ambient temperature before submitting for NMR analysis to determine the extent of reaction.

The above synthesis was repeated with 2-ME (0.4 mol), solid HMTA (0.2 mol) and water (50% of composition) heated for about 2 h at about 100-105° C. at which time the mixture was homogeneous and the solution was cooled and submitted for analysis.

The above synthesis was repeated with 2-ME (0.60 mol), solid HMTA (0.20 mol) and water (50% of composition) heated for about 3 h at about 100-110° C. at which time the mixture was homogeneous and the solution was cooled and submitted for analysis.

The above synthesis was repeated with 2-ME (0.80 mol), solid HMTA (0.20 mol) and water (50% of composition) heated for about 3 h at about 100-110° C. at which time the mixture was homogeneous and the solution was cooled and submitted for analysis.

The above synthesis was repeated with 2-ME (1 mol), solid HMTA (0.2 mol) and water (50% of composition) heated for about 3 h at about 90-107° C. at which time the mixture was homogeneous and the solution was cooled and submitted for analysis.

The above synthesis was repeated with 2-ME (1.2 mol), solid HMTA (0.2 mol) and water (50% of composition) heated for about 4 h at about 90-105° C. at which time the mixture was homogeneous and the solution was cooled and submitted for analysis.

Under normal atmospheric conditions, 2-ME (4 mol) was stirred and heated to 70-75° C. and solid HMTA (1 mol) was slowly added via a solid addition funnel to a suitable volume round bottom flask equipped with a reflux condenser and a magnetic stir bar. The slurry was heated to 80-120° C. under stirring for about 4 h at which time the mixture was homogeneous. The solution was allowed to cool to ambient temperature before submitting for NMR analysis to determine the extent of reaction.

The above synthesis was repeated with 2-ME (1 mol) heated to about 100° C. and solid HMTA (0.25 mol) added and heated for about 2 h at about 120° C. at which time the mixture was homogeneous and the solution was cooled and submitted for analysis.

The above synthesis was repeated with 2-ME (4.0 mol) heated to 80-100° C. and powdered HMTA solid (1.0 mol) was added slowly with solids addition funnel and heated with stirring for about 2 h at 100-120° C. until the mixture was homogeneous. The sample was cooled and submitted for analysis.

The synthesis was repeated with ammonium hydroxide (28.0%, 0.36 mol) heated to 60-75° C. with stirring and 2-ME-formaldehyde addition product (1.10 mol) taken into an addition funnel was slowly added and continued heating while stirring for about 2 h at 70-75° C. The reaction was monitored by FTIR. The sample was cooled and submitted for C13-NMR and LC-MS.

C-13 NMR and LC-MS confirmed that the composition of HMTA and 2-ME reaction products with and without water gave the same reaction products, with variation in composition depending on 2-ME and HMTA ratios.

The LC-MS results showed that the reaction products generated from reaction of ammonium hydroxide and 2-ME-formaldehyde addition product were the same those generated from HMTA+2-ME reaction.

A synthesis was carried out with 2-ME (1.0 mol) heated to 80-100 C and powdered HMTA solid (0.25 mol) was added slowly with solids addition funnel and heated with stirring for about 2 h at 120-130° C. until the mixture is homogeneous. Phosphate ester of NPE-9 was slowly added and continued heating with stirring and nitrogen sweep. No water came over but the reaction mixture was clear. After 2.5 h at 120-130° C., heating was stopped and the product was cooled and bottled for analysis and testing.

Example 2: Reaction of TGA with HMTA

Under normal atmospheric conditions, TGA (0.576 mol) is stirred and heated to 90-95° C. and powdered HMTA solid (0.144 mol) is slowly added via a solid addition funnel to a suitable volume round bottom flask equipped with a reflux condenser and a magnetic stir bar. The slurry was heated to 120° C. under stirring for about 2 h at which time the mixture was homogeneous. The solution was allowed to cool to ambient temperature before submitting for NMR analysis to determine the extent of reaction.

The above synthesis was repeated with TGA (4 mol) heated to about 100° C. and powdered HMTA solid (1 mol) added and heated for about 2.5 h at about 120° C. at which time the mixture was homogeneous and the solution was cooled and submitted for analysis.

The above synthesis was repeated with TGA (1 mol) heated to about 85° C. and powdered HMTA solid (0.125 mol) added and heated for about 3.5 h at about 120° C. at which time the mixture was homogeneous and the solution was cooled and submitted for analysis.

The above synthesis was repeated with TGA (4.0 mol) heated to 80-100° C. and powdered HMTA solid (1.0 mol) was added slowly with solids addition funnel and heated with stirring for about 2 h at 100-120° C. until the mixture was homogeneous. The sample was cooled and submitted for analysis.

Example 3: Corrosion Bubble Cell Tests

Thiol-amine compounds A and B (having a 2-ME:HMTA molar ratio of 4:1 and a TGA:HMTA molar ratio of 4:1, respectively) were evaluated for corrosion performance as compared to TGA and 2-ME via a bubble test procedure. The bubble test simulates low flow areas where little or no mixing of water and oil occurs. The test was conducted using brine (80% of the brine being 3% sodium chloride brine and 20% of the brine being a hydrocarbon containing 75% LVT-200 and 25% xylene). The brine was placed into kettles and purged with carbon dioxide. The brine was continually purged with carbon dioxide to saturate the brine prior to starting the test. After the test began, the test cell was blanketed with carbon dioxide one hour prior to electrode insertion and through the duration of the test to maintain saturation. The kettles were stirred at 150 revolutions per minute (rpm) for the duration of the test to maintain thermal equilibrium at 80° C. The corrosion rate was measured by Linear Polarization Resistance (LPR) techniques. The working electrode used was carbon steel. The counter and reference electrodes were both 1018 carbon steel. The electrodes were all cleaned and polished prior to testing. Data were collected for three hours before 10 ppm of each of the compositions was dosed into its respective cell. Data were collected overnight.

The results of the bubble test are shown in Table 1, wherein ppm is parts per million, CI is corrosion inhibitor, and mpy is mils per year.

TABLE 1

| Candidate Synergist Chemistry | Dosage of corrosion inhibitor blend (ppm) | Average Baseline before CI addition (mpy) | Inhibited corrosion rate 15 h after CI addition (mpy) |
|---|---|---|---|
| None | 0 | 260 | 500 |
| TGA | 10 | 241 | 294 |
| 2-ME | 10 | 238 | 123 |
| Compound Mixture A (2-ME/HMTA 4:1) | 10 | 237 | 128 |
| Compound Mixture B (TGA/HMTA 4:1) | 10 | 238 | 154 |

Example 4: Headspace Tests

In order to illustrate the added benefit of the compounds for decreasing the evolution of volatile sulfur-containing degradation components, headspace measurements were performed on example corrosion inhibitor compounds. The headspace measurements were performed in accordance with the standard ASTM-D 5705 method. Briefly, the method used for this screening is to place 40 g of the corrosion inhibitor compound into an 8 ounce glass jar sealed with a cap containing a hole fitted with a rubber stopper which is used for sampling. The samples were subsequently aged in a 50° C. oven over the specified period of hours before sampling. Samples were analyzed by removal of the rubber stopper and the headspace was subsequently sampled using GasTec sulfur detection tubes.

Four headspace tests were performed with samples of TGA, 2-ME, TGA and HMTA in a 4:1 weight ratio, and 2-ME and HMTA in a 4:1 weight ratio. The results of headspace evaluation experiments for each of the four samples stored at 50° C. for various periods of time are shown in Table 2.

TABLE 2

| | Headspace $H_2S$ evolution at 50° C. (ppm) | | | |
|---|---|---|---|---|
| Chemistry | 65 h | 184 h | 233 h | 639 h |
| Thioglycolic acid (TGA) | — | >4,000* | — | — |
| 2 mercaptoethanol (2-ME) | — | 2,500 | — | — |
| 2-ME/HMTA (4:1) | ND | — | ND | ND |
| TGA/HMTA (4:1) | ND | — | ND | ND |

*The measurement exceeded the 4,000 ppm maximum range
—: no measurement taken
ND: Non-detectable amounts of hydrogen sulfide The terms "comprise(s)," "include(s)," "having," "has," "can," "contain(s)," and variants thereof, as used herein, are intended to be open-ended transitional phrases, terms, or words that do not preclude the possibility of additional steps or components. The singular forms "a," "and," "the" and "said" include plural references unless the context clearly dictates otherwise. The present disclosure also contemplates other embodiments "comprising," "consisting of" and "consisting essentially of," the embodiments or elements presented herein, whether explicitly set forth or not.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A compound having the formula:

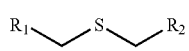  (1)

wherein:
Each $R_1$ is independently —$CH_2OH$ and —$C(O)OH$;
$R_2$ is

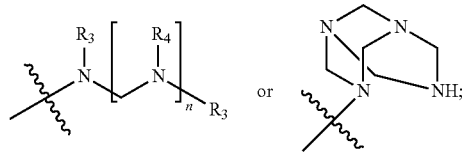

Each $R_3$ is independently hydrogen or $R_5$, or both $R_3$ together form a ring via a linker

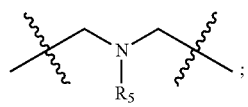

Each $R_4$ is independently hydrogen or $R_5$;
$R_5$ is —$CH_2SC_2H_4R_1$; and
n is an integer from 0 to 3;
wherein the compound is other than:

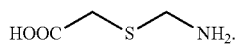

2. The compound of claim 1, having the formula:

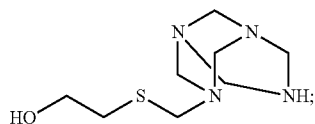  (2)

3. The compound of claim 1, having the formula:

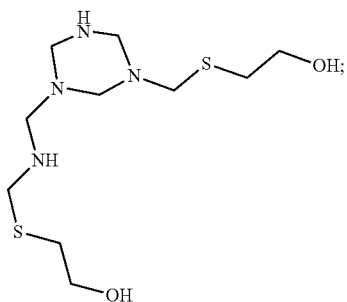  (3)

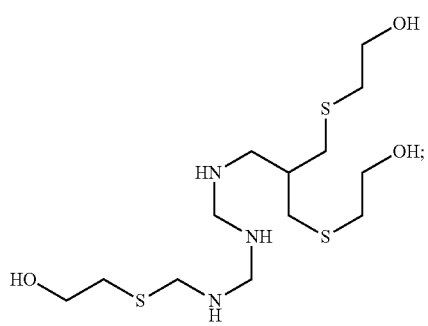  (4)

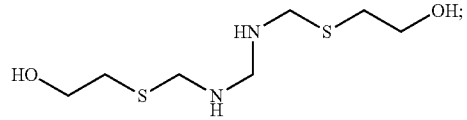  (5)

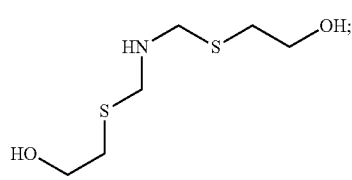  (6)

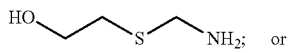  (7)

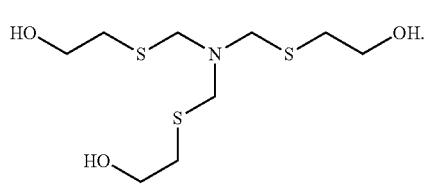  (8)

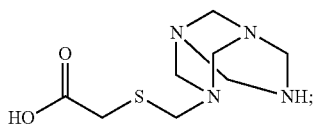  (9)

-continued

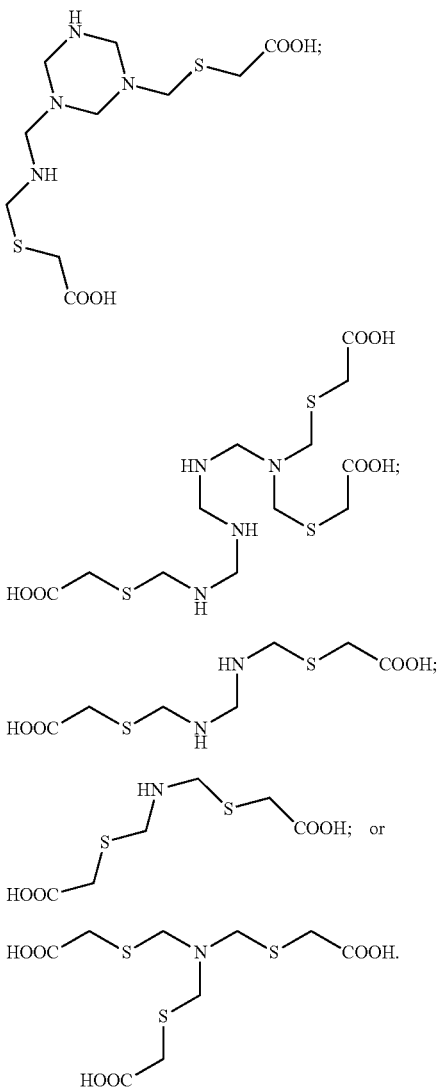

4. A composition for inhibiting corrosion at a surface, the composition comprising a compound of claim 1 and a component selected from the group consisting of a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, an organic solvent or a combination thereof.

5. The composition of claim 4, wherein the organic solvent is selected from the group consisting of an alcohol, a hydrocarbon, a ketone, an ether, an alkylene glycol, a glycol ether, an amide, a nitrile, a sulfoxide, an ester, or a combination thereof, and the composition optionally comprises water.

6. The composition of claim 4, wherein the organic solvent is selected from the group consisting of methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

7. The composition of claim 4, wherein the corrosion inhibitor is selected from the group consisting of an imidazoline compound, a quaternary ammonium compound, a pyridinium compound or a combination thereof.

8. The composition of claim 4, comprising from about 0.1 to about 20 wt. % of the compound.

9. A method of inhibiting corrosion at a surface comprising contacting the surface with a composition comprising a compound of claim 1.

10. The method of claim 9, wherein the compound has the formula:

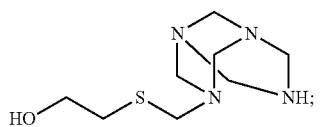
(2)

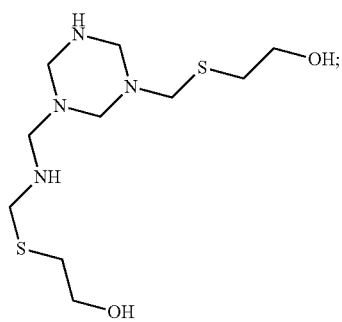
(3)

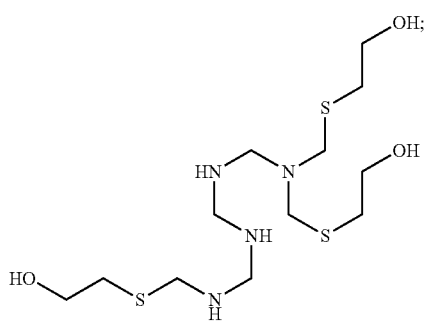
(4)

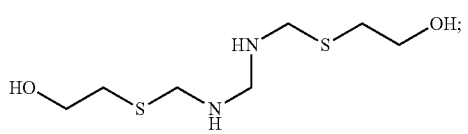
(5)

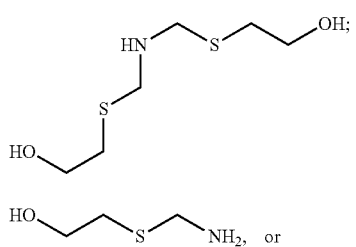
(6)

(7)

-continued

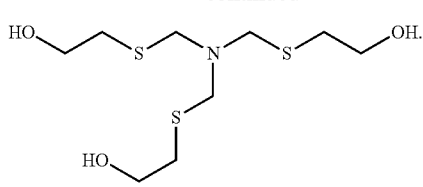 (8)

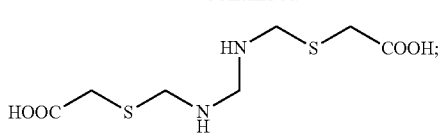 (12)

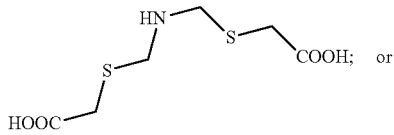 (13)

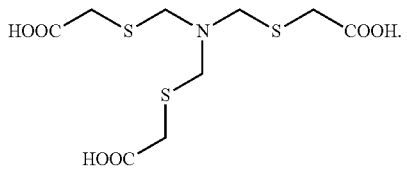 (15)

11. The method of claim 9, wherein the compound has the formula:

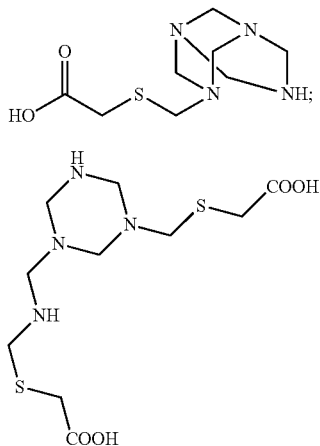 (9)

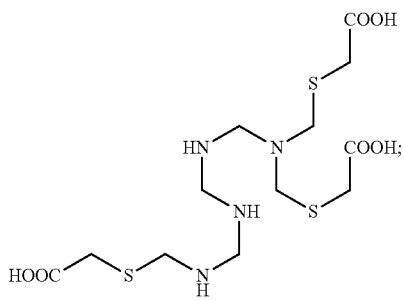 (10)

(11)

12. The method of claim 9, wherein the surface is part of a wellbore or equipment used in the production, transportation, storage, and/or separation of the fluid.

13. The method of claim 9, wherein the surface is part of equipment used in a coal-fired process, a waste-water process, a farm, a slaughter house, a land-fill, a municipality waste-water plant, a coking coal process, or a biofuel process.

14. The method of claim 12, wherein the equipment comprises a pipeline, a storage vessel, downhole injection tubing, a flow line, or an injection line.

15. The method of claim 9, wherein the composition comprises from about 0.1 to about 20 wt. % of the compound.

* * * * *